United States Patent [19]

Winter

[11] Patent Number: 5,225,539
[45] Date of Patent: Jul. 6, 1993

[54] RECOMBINANT ALTERED ANTIBODIES AND METHODS OF MAKING ALTERED ANTIBODIES

[75] Inventor: Gregory P. Winter, Cambridge, United Kingdom

[73] Assignee: Medical Research Council, London, England

[21] Appl. No.: 782,717

[22] Filed: Oct. 25, 1991

Related U.S. Application Data

[63] Continuation of Ser. No. 903,776, Mar. 27, 1986, abandoned.

[30] Foreign Application Priority Data

Mar. 27, 1986 [GB] United Kingdom ............... 8607679

[51] Int. Cl.$^5$ .................. C07K 15/28; A61K 39/395; C12N 5/12; C12N 15/13
[52] U.S. Cl. ................................ 530/387.3; 424/85.8; 424/85.91; 435/69.6; 435/70.21; 435/172.2; 435/172.3; 435/240.27; 435/252.3; 435/252.33; 435/320.1; 935/100; 935/104; 935/107
[58] Field of Search ................. 530/387.3, 388.15; 424/85.8, 85.91; 435/69.1, 69.6, 69.7, 70.21, 172.2, 172.3, 240.27, 252.3, 252.33, 320.1; 935/70, 71, 100, 102, 104, 107

[56] References Cited

FOREIGN PATENT DOCUMENTS 125023  11/1984  European Pat. Off. .
173494  3/1986   European Pat. Off. .
183964  6/1986   European Pat. Off. .
184187  6/1986   European Pat. Off. .
WO8601533 3/1986 PCT Int'l Appl. .
8601533 3/1986  PCT Int'l Appl. ................ 530/387

OTHER PUBLICATIONS

Morrison et al., PNAS, 81, 6851-5, (Nov. 1984).
Rechavi et al., PNAS, 82, 4405-9 (Jul. 1982).
Sahasan et al., J. Immunol., 137, (3), 1066-74, (1986).
Kabat et al., Sequences of Proteins of Immunol Interest, pp. i-xx, (1983).
Nose et al., PNAS, 80, 6632-6, (Nov. 1983).
Kabat, Adv. Prot. Chem., vol. 32, pp. 2-75, (1978) (New York).
Boulianne et al., Nature, 312, 643-46, (Dec. 1984).
Kabat et al., J. Exp. Med., 149, 1299-1313, (1979).
Oi et al., P.N.A.S., 80, 825-29, (1983).
Wu et al., P.N.A.S., 79, 5031-2, (1982).
Ochi et al., P.N.A.S., 80, 6351-55, (1983).
Julius et al., Mol. Immunol, 18, 1-9, (1981).
Brugëmann et al., EMBO J., 1(5), 629-34, (1982).
Neuberger et al., Nature, 314, 268-70, 21 Mar. 1985.
Chothia et al., J. Mol. Biol. 196, 901-917 (1987).
Amit et al., Science 233, 747-753 (1986).
Ward et al., Nature 341, 544-546 (1989).
Hudson et al., J. Immunology 139, 2715-2723 (1987).
Suh et al., Proteins 1, 74-80 (1986).
Padlan et al., PNAS USA 86, 5938-5942 (1989).
Lesk et al., J. Mol. Biol. 160, 325-342 (1982).
Padlan et al., Cold Spring Harbor Symp. Quant. Biol. 41, 627-637 (1976).
Colman et al., Nature 326, 358-363 (1987).
Riechmann et al., Nature 332, 323-327 (1988).
Hale et al., Lancet 1394-1399 (1988).
Jaffers et al., Transplantation 41, 572-578 (1986).
Queen et al., PNAS, in press (1989).
Fersht, A. et al., Hydrogen Binding and Biological Specificity Analysed by Protein Engineering, Nature vol. 314, Mar. 1985, pp. 235-238.
Williams, W. V. et al., Development of Biologically Active Peptides Based on Antibody Structure, Proc. Natl. Acad. Sci. USA vol. 86, Jul. 1989, pp. 5537-5541.
Taub, R. et al., A Monoclonal Antibody Against the Platelet Fibrinogen Receptor Contains A Sequence ..., J. Biol. Chem. vol. 264, pp. 259-265.
R. W. Old et al., "Principles of Gene Manipulation", Blackwell Scientific Publications, pp. 99 to 101 (1980).
Alan Munro, "Uses of chimaeric antibodies", Nature, vol. 312, p. 597 (Dec. 13, 1984).

Primary Examiner—David L. Lacey
Assistant Examiner—Robert D. Budens
Attorney, Agent, or Firm—Spencer, Frank & Schneider

[57] ABSTRACT

An altered antibody is produced by replacing the complementarity determining regions (CDRs) of a variable region of an immunoglobulin (Ig) with the CDRs from an Ig of different specificity, using recombinant DNA techniques. The gene coding sequences for producing the altered antibody may be produced by site-directed mutagenesis using long oligonucleotides.

23 Claims, 5 Drawing Sheets

```
                        FR1                                                    CDR1
         1                                    30                          31        35
NEWM    XVQLQESGPGLVRPSQTLSLTCTVSGSTFS              NEWM                    NDYYT
B1-8    QVQLQQPGAELVKPGASVKLSCKASGYTFT              B1-8                    SYWMH

FR2                                           CDR2
         36              49                          50                          65
NEWM    WVRQPPGRGLEWIG                              NEWM    YVFYHGTSDDTTPLRS
B1-8    WVKQRPGRGLEWIG                              B1-8    RIDPNSGGTKYNEKFKS

FR3                                         CDR3
         66                                    94    95              102
NEWM    RVTMLVDTSKNQFSLRLSSVTAADTAVYYCAR       NEWM    NLIAGCIDV
B1-8    KATLTVDKPSSTAYMQLSSLTSEDSAVYYCAR       B1-8    YDYYGSSYFDY

FR4
         103       113
NEWM    WGQGSLVTVSS
B1-8    WGQGTTLTVSS
```

```
        HindIII  -48              -23          -7
     ↓                     ____         ____       ____
5'..........ATGCAAATCCTCTGAATCTACATGGTAAATATAGGTTTGTCTATAC
      ■→ RNA starts      ■→ RNA starts
   CACAAACAGAAAAACATGAGATCACAGTTCTCTCTACAGTTACTGAGCACACAGGACCTC
                    NP leader                          Splice
         ┌─────────────────────────────────────────┐   ↓
         │ M  G  W  S  C  I  I  L  F  L  V  A  T  A  T │
   ACCATGGGATGGAGCTGTATCATCCTCTTCTTGGTAGCAACAGCTACAGGTAAGGGGCTC ACAGTAGCAGGCTTGAGGTCTGGACATATATATGGGTGACAATGACATCCACTTTGCCTT
      Splice        1                  5    PstI    10
        ↓ G  V  H  S  Q  V  Q  L  Q ↓ E  S  G  P  G  L  V  R
   TCTCTCCACAGGTGTCCACTCCCAGGTCCAACTGCA GGAGAGCGGTCCAGGTCTTGTGAG
                                      5'└──────1──────┘
                                    3'┌──────2──────┐ ┌─
         15            20           25          30     CDR1
                                                       ┌─────┐
    P  S  Q  T  L  S  L  T  C  T  V  S  G  S  T  F  S │ S  Y  W │
   ACCTAGCCAGACCCTGAGCCTGACCTGCACCGTGTCTGGCAGCACCTTCAGCAGCTACTG
         └──3──┘┌──────┐          └──5──┐ ┌─────┐  └─7─
    ─┐  ┌──4──┐                  ┌──6──┘            ─8──
          35           40            45         50 CDR2  52A
    ┌─────┐                                        ┌────────┐
    │ M  H │ W  V  R  Q  P  P  G  R  G  L  E  W  I  G │ R  I  D  P │
   GATGCACTGGGTGAGACAGCCACCTGGACGAGGTCTTGAGTGGATTGGAAGGATTGATCC
     ──7──┘ └──────9a──────┘ └──9b──┘  └──11──
        ┌──10a──┐ ┌──10b──┐             ┌──12/14──
         55   CDR2     60              65           70
        ┌──────────────────────────────────┐
    │ M  S  G  G  T  K  Y  N  E  K  F  K  S │ R  V  T  M  L  V  D
   TAATAGTGGTGGTACTAAGTACAATGAGAAGTTCAAGAGCAGAGTGACAATGCTGGTAGA
    ──11──┘ └──13a──┘ └──13b──┘ └──15──
       ┌──12/14──────┐                 ┌──16──
         75            80    82A B  C      85
    T  S  K  N  Q  F  S  L  R  L  S  S  V  T  A  A  D  T  A  V
   CACCAGCAAGAACCAGTTCAGCCTGAGACTCAGCAGCGTGACAGCCGCCGACACCGCGGT
     ──15──┘  └──17──────┘                  └──19──
       ┌──18──────┐                     ┌──20──
         90           95  CDR3        100A B C         105
                         ┌──────────────────────────┐
    Y  Y  C  A  R │ Y  D  Y  Y  G  S  S  Y  F  D  Y │ W  G  Q  G
   CTATTATTGTGCAAGATACGATTACTACGGTAGTAGCTACTTTGACTACTGGGGTCAAGG
     ──19──┘  └──21──┘               └──23──┘ └─
       ┌──────22/24──────┐                  ┌──26a──
         110          Splice               BamHI
    S  L  V  T  V  S  S │ ↓                 ↓
   CAGCCTCGTCACAGTCTCCTCAGGT.......193bp....3'
     ──25──── GACA 3'
    ┐┌──26b── CTGTTCGA 5'
```

Fig. 5
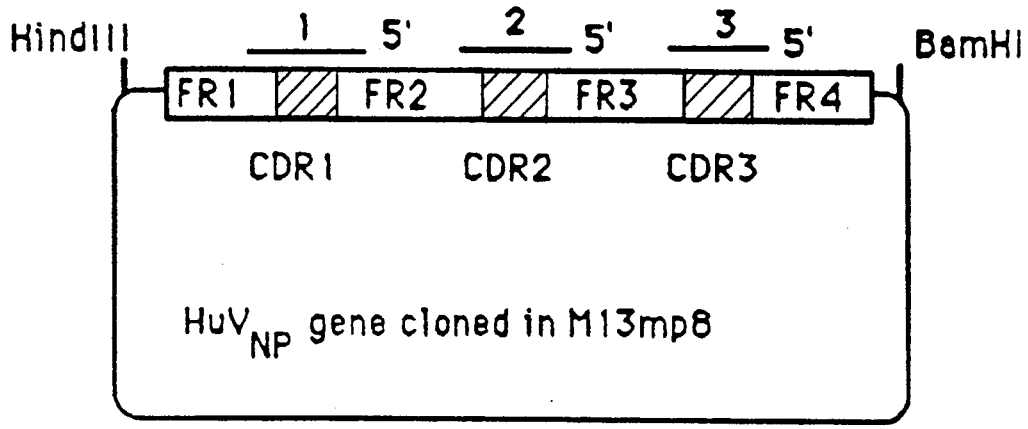
D1.3 CDR1 oligonucleotide
5' CTG,TCT,CAC,CCA,GTT,TAC,ACC,ATA,GCC,GCT,GAA,GGT,GCT
FR2        D1.3 CDR1        FR1
D1.3 CDR2 oligonucleotide
5' CAT,TGT,CAC,TCT,GGA,TTT,GAG,AGC,TGA,ATT,ATA,GTC,TGT,
FR3        D1.3 CDR2
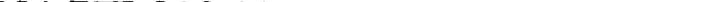
GTT,TCC,ATC,ACC,CCA,AAT,CAT,TCC,AAT,CCA,CTC
D1.3 CDR2        FR2
D1.3 CDR3 oligonucleotide
5' GCC,TTG,ACC,CCA,GTA,GTC,AAG,CCT,ATA,ATC,TCT,CTC,TCT,
FR4        D1.3 CDR3
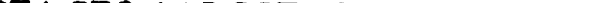
TGC,ACA,ATA
FR3

RECOMBINANT ALTERED ANTIBODIES AND METHODS OF MAKING ALTERED ANTIBODIES

This application is a continuation of U.S. patent application Ser. No. 06/903,776, filed Mar. 27, 1986, now abandoned.

The present invention relates to altered antibodies in which the complementarity determining regions (CDRs) in the light or heavy chain variable domains of the antibody have been replaced by the analogous CDRs from an antibody of different specificity. The present invention also relates to methods for the production of such altered antibodies.

Natural antibodies, or immunoglobulins, comprise two heavy chains linked together by disulphide bonds and two light chains, one light chain being linked to each of the heavy chains by disulphide bonds. Each heavy chain has at one end a variable domain followed by a number of constant domains. Each light chain has a variable domain at one end and a constant domain at its other end, the variable domain being aligned with the variable domain of the heavy chain and the constant domain being aligned with the first constant domain of heavy chain.

The constant domains in the light and heavy chains are not involved directly in binding the antibody to the antigen. The general structure of an antibody of class IgG (i.e. an immunoglobulin (Ig) of class gamma (G)) is shown schematically in FIG. 1 of the accompanying drawings.

The variable domains of each pair of light and heavy chains form the antigen binding site. The domains on the light and heavy chains have the same general structure and each domain comprises four framework regions, whose sequences are relatively conserved, connected by three hypervariable or complementarity determining regions (CDRs) (see Kabat, E. A., Wu, T. T., Bilofsky, H., Reid-Miller, M. and Perry, H., in "Sequences of Proteins of Immunological Interest", US Dept. Health and Human Services 1983). The four framework regions largely adopt a $\beta$-sheet conformation and the CDRs form loops connecting, and in some cases forming part of, the $\beta$-sheet structure. The CDRs are held in close proximity by the framework regions and with the CDRs from the other domain contribute to the formation of the antigen binding site.

For a more detailed account of the structure of variable domains, reference may be made to: Poljak, R. J., Amzel, L. M., Avey, H. P., Chen, B. L., Phizackerly, R. P. and Saul, F., PNAS USA, 70, 3305-3310, 1973; Segal, D. M., Padlan, E. A., Cohen, G. H., Rudikoff, S., Potter, M. and Davies, D. R., PNAS USA, 71, 4298-4302, 1974; and Marquart, M., Deisenhofer, J., Huber, R. and Palm, W., J. Mol. Biol., 141, 369-391, 1980.

In recent years advances in molecular biology based on recombinant DNA techniques have provided processes for the production of a wide range of heterologous polypeptides by transformation of host cells with heterologous DNA sequences which code for the production of the desired products.

EP-A-0 088 994 (Schering Corporation) proposes the construction of recombinant DNA vectors comprising a ds DNA sequence which codes for a variable domain of a light or a heavy chain of an Ig specific for a predetermined ligand. The ds. DNA sequence is provided with initiation and termination codons at its 5'- and 3'-termini respectively, but lacks any nucleotides coding for amino acids superfluous to the variable domain. The ds DNA sequence is used to transform bacterial cells. The application does not contemplate variations in the sequence of the variable domain.

EP-A-1 102 634 (Takeda Chemical Industries Limited) describes the cloning and expression in bacterial host organisms of genes coding for the whole or a part of human IgE heavy chain polypeptide, but does not contemplate variations in the sequence of the polypeptide.

EP-A-0 125 023 (Genentech Inc.) proposes the use of recombinant DNA techniques in bacterial cells to produce Ig's which are analogous to those normally found in vertebrate systems and to take advantage of the gene modification techniques proposed therein to construct chimeric Ig's or other modified forms of Ig.

The term 'chimeric antibody' is used to describe a protein comprising at least the antigen binding portion of an immunoglobulin molecule (Ig) attached by peptide linkage to at least part of another protein.

It is believed that the proposals set out in the above Genentech application did not lead to the expression of any significant quantities of Ig polypeptide chains, nor to the production of Ig activity, nor to the secretion and assembly of the chains into the desired chimeric Ig's.

The production of monoclonal antibodies was first disclosed by Kohler and Milstein (Kohler, G. and Milstein, C., Nature, 256, 495-497, 1975). Such monoclonal antibodies have found widespread use not only as diagnostic reagents (see, for example, 'Immunology for the 80s, Eds. Voller, A., Bartlett, A., and Bidwell, D., MTP Press, Lancaster, 1981) but also in therapy (see, for example, Ritz, J. and Schlossman, S. F., Blood, 59, 1-11, 1982).

The recent emergence of techniques allowing the stable introduction of Ig gene DNA into myeloma cells (see, for example, Oi, V. T., Morrison, S. L., Herzenberg, L. A. and Berg, P., PNAS USA, 80, 825-829, 1983; Neuberger, M. S., EMBO J., 2, 1373-1378, 1983; and Ochi, T., Hawley, R. G., Hawley, T., Schulman, M. J., Traunecker, A., Kohler, G. and Hozumi, N., PNAS USA, 80, 6351-6355, 1983), has opened up the possibility of using in vitro mutagenesis and DNA transfection to construct recombinant Ig's possessing novel properties.

However, it is known that the function of an Ig molecule is dependent on its three dimensional structure, which in turn is dependent on its primary amino acid sequence. Thus, changing the amino acid sequence of an Ig may adversely affect its activity. Moreover, a change in the DNA sequence coding for the Ig may affect the ability of the cell containing the DNA sequence to express, secrete or assemble the Ig.

It is therefore not at all clear that it will be possible to produce functional altered antibodies by recombinant DNA techniques.

However, colleagues of the present Inventor have devised a process whereby chimeric antibodies in which both parts of the protein are functional can be secreted. The process, which is disclosed in International Patent Application No. PCT/GB85/00392 (Neuberger et al. and Celltech Limited), comprises:

a) preparing a replicable expression vector including a suitable promoter operably linked to a DNA sequence comprising a first part which encodes at least the variable domain of the heavy or light chain of an Ig molecule and a second part which encodes at least part of a second protein;

b) if necessary, preparing a replicable expression vector including a suitable promoter operably linked to a DNA sequence which encodes at least the variable domain of a complementary light or heavy chain respectively of an Ig molecule;

c) transforming an immortalised mammalian cell line with the or both prepared vectors; and d) culturing said transformed cell line to produce a chimeric antibody.

The second part of the DNA sequence may encode:

i) at least part, for instance the constant domain of a heavy chain, of an Ig molecule of different species, class or subclass;

ii) at least the active portion or all of an enzyme;

iii) a protein having a known binding specificity;

iv) a protein expressed by a known gene but whose sequence, function or antigenicity is not known; or v) a protein toxin, such as ricin.

The above Neuberger application only shows the production of chimeric antibodies in which complete variable domains are coded for by the first part of the DNA sequence. It does not show any chimeric antibodies in which the sequence of the variable domain has been altered.

The present invention, in a first aspect, provides an altered antibody in which at least parts of the CDRs in the light or heavy chain variable domains have been replaced by the analogous CDRs from an antibody of different specificity.

The entire CDRs may be replaced. Alternatively, only those parts of the CDRs critical for antigen binding may be replaced.

Preferably, the variable domains in both the heavy and light chains have been altered by CDR replacement.

Although the CDRs may be derived from an antibody of the same class or even subclass as the antibody from which the framework regions are derived, it is envisaged that the CDRs will be derived from an antibody of different class and preferably from an antibody from a different species.

Thus, it is envisaged, for instance, that the CDRs from a mouse antibody could be grafted onto the framework regions of a human antibody. This arrangement will be of particular use in the therapeutic use of monoclonal antibodies.

At present, when a mouse monoclonal antibody or even a chimeric antibody comprising a complete mouse variable domain is injected into a human, the human body's immune system recognises the mouse variable domain as foreign and produces an immune response thereto. Thus, on subsequent injections of the mouse antibody or chimeric antibody into the human, its effectiveness is considerably reduced by the action of the body's immune system against the foreign antibody. In the altered antibody of the present invention, only the CDRs of the antibody will be foreign to the body, and this should minimise side effects if used for human therapy. Although, for example, human and mouse framework regions have characteristic sequences, there seems to be no characteristic features which distinguish human from mouse CDRs. Thus, an antibody comprised of mouse CDRs in a human framework may well be no more foreign to the body than a genuine human antibody.

Preferably, the altered antibody has the structure of a natural antibody or a fragment thereof. Thus, the altered antibody may comprise a complete antibody, an (Fab')2 fragment, an Fab fragment, a light chain dimer or a heavy chain dimer.

Alternatively, the altered antibody may be a chimeric antibody of the type referred to in the Neuberger application referred to above. The production of such an altered chimeric antibody can be carried out using the methods described below used in conjunction with the methods described in the Neuberger application.

The present invention, in a second aspect, comprises a method for producing such an altered antibody comprising:

a) preparing a first replicable expression vector including a suitable promoter operably linked to a DNA sequence which encodes at least a variable domain of an Ig heavy or light chain, the variable domain comprising framework regions from a first antibody and CDRs comprising at least parts of the CDRs from a second antibody of different specificity;

b) if necessary, preparing a second replicable expression vector including a suitable promoter operably linked to a DNA sequence which encodes at least the variable domain of a complementary Ig light or heavy chain respectively;

c) transforming a cell line with the first or both prepared vectors; and d) culturing said transformed cell line to produce said altered antibody.

The present invention also includes vectors used to transform the cell line, vectors used in producing the transforming vectors, cell lines transformed with the transforming vectors, cell lines transformed with preparative vectors, and methods for their production.

Preferably, the cell line which is transformed to produce the altered antibody is an immortalised mammalian cell line, which is advantageously of lymphoid origin, such as a myeloma, hybridoma, trioma or quadroma cell line. The cell line may also comprise a normal lymphoid cell, such as a B-cell, which has been immortalised by transformation with a virus, such as the Epstein-Barr virus. Most preferably, the immortalised cell line is a myeloma cell line or a derivative thereof.

Although the cell line used to produce the altered antibody is preferably a mammalian cell line, any other suitable cell line, such as a bacterial cell line or a yeast cell line, may alternatively be used. In particular, it is envisaged that *E. coli* derived bacterial strains could be used.

It is known that some immortalised lymphoid cell lines, such as myeloma cell lines, in their normal state, secrete isolated Ig light or heavy chains. If such a cell line is transformed with the vector prepared in step a) of the process of the invention, it will not be necessary to carry out step b) of the process, provided that the normally secreted chain is complementary to the variable domain of the Ig chain encoded by the vector prepared in step a).

However, where the immortalised cell line does not secrete or does not secrete a complementary chain, it will be necessary to carry out step b). This step may be carried out by further manipulating the vector produced in step a) so that this vector encodes not only the variable domain of the Ig chain second protein, but also the complementary variable domain. However, preferably step b) is carried out by preparing a second vector which is used to transform the immortalised cell line.

The techniques by which such vectors can be produced and used to transform the immortalised cell lines are well known in the art, and do not form any part of the invention.

In the case where the immortalised cell line secretes a complementary light or heavy chain, the transformed cell line may be produced for example by transforming a suitable bacterial cell with the vector and then fusing the bacterial cell with the immortalised cell line by spheroplast fusion). Alternatively, the DNA may be directly introduced into the immortalised cell line by electroporation.

The DNA sequence encoding the altered variable domain may be prepared by oligonucleotide synthesis. This requires that at least the framework region sequence of the first antibody and at least the CDRs sequences of the second antibody are known or can be readily determined. Although determining these sequences, the synthesis of the DNA from oligonucleotides and the preparation of suitable vectors is to some extent laborious, it involves the use of known techniques which can readily be carried out by a person skilled in the art in light of the teaching given here.

Alternatively, the DNA sequence encoding the altered variable domain may be prepared by primer directed oligonucleotide site-directed mutagenesis. This technique in essence involves hybridising an oligonucleotide coding for a desired mutation with a single strand of DNA containing the mutation point and using the single strand as a template for extension of the oligonucleotide to produce a strand containing the mutation. This technique, in various forms, is described by: Zoller, M. J. and Smith, M., Nuc. Acids Res., 10, 6487-6500, 1982; Norris, K., Norris F., Christiansen, L. and Fiil, N., Nuc. Acids res., 11, 5103-5112, 1983; Zoller, M. J. and Smith, M., DNA, 3, 479-488 (1984); Kramer, W., Schughart, K. and Fritz, W. -J., Nuc. Acids Res., 10, 6475-6485, 1982.

For various reasons, this technique in its simplest form does not always produce a high frequency of mutation. An improved technique for introducing both single and multiple mutations in an M13 based vector, has been described by Carter et al. (Carter, P., Bedouelle H. and Winter, G., Nuc. Acids Res., 13, 4431-4443, 1985).

Using a long oligonucleotide, it has proved possible to introduce many changes simultaneously (as in Carter et al., loc. cit.) and thus single oligonucleotides, each encoding a CDR, can be used to introduce the three CDRs from the second antibody into the framework regions of the first antibody. Not only is this technique less laborious than total gene synthesis, but it represents a particularly convenient way of expressing a variable domain of required specificity, as it can be simpler than tailoring an entire $V_H$ domain for insertion into an expression plasmid.

The oligonucleotides used for site-directed mutagenesis may be prepared by oligonucleotide synthesis or may be isolated from DNA coding for the variable domain of the second antibody by use of suitable restriction enzymes. Such long oligonucleotides will generally be at least 30 residues long and may be up to or over 80 residues in length.

The techniques set out above may also be used, where necessary, to produce the vector of part (b) of the process.

The method of the present invention is envisaged as being of particular use in "humanising" non-human monoclonal antibodies. Thus, for instance, a mouse monoclonal antibody against a particular human cancer cell may be produced by techniques well known in the art. The CDRs from the mouse monoclonal antibody may then be grafted into the framework regions of a human monoclonal antibody, which is then produced in quantity by a suitable cell line. The product is thus a specifically targetted, essentially human antibody which will recognise the cancer cells, but will not itself be recognised, to any significant degree, by a human's immune system. Thus, the method and product of the present invention will be of particular use in the clinical environment.

The present invention is now described, by way of example only, with reference to the accompanying drawings, in which:

FIG. 2 shows the amino acid sequence of the $V_H$ domain of NEWM in comparison with the $V_H$ domain of the BI-8 antibody;

FIG. 3 shows the amino acid and nucleotide sequence of the $HuV_{NP}$ gene;

FIG. 5 shows the structure of three oligonucleotides used for site directed mutagenesis.

EXAMPLE 1

Figure 1:
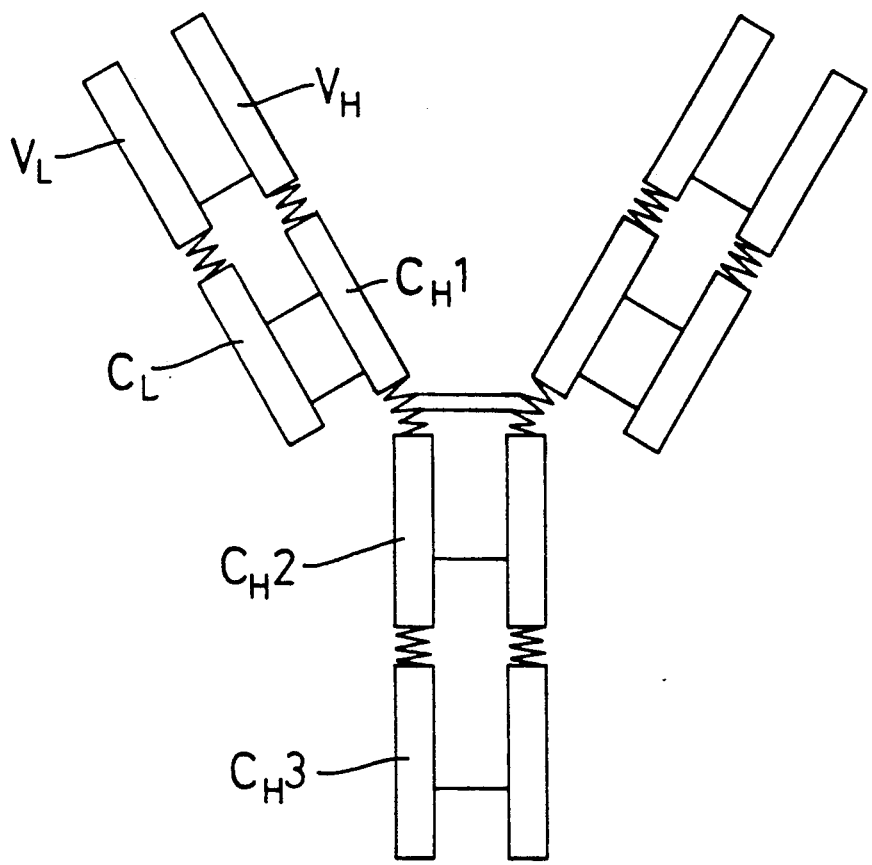
FIG. 1 is a schematic diagram showing the structure of an IgG molecule.

This example shows the production of an altered antibody in which the variable domain of the heavy chains comprises the framework regions of a human heavy chain and the CDRs from a mouse heavy chain.

The framework regions were derived from the human myeloma heavy chain NEWM, the crystallographic structure of which is known (see Poljak et al., loc. cit. and, Bruggemann, M., Rodbruch, A. and Rajewsky, K., EMBO J., 1, 629–634, 1982.)

The CDRs were derived from the mouse monoclonal antibody B1-8 (see Reth et al., loc. cit.), which binds the hapten NP-cap (4-hydroxy-3-nitrophenylacetyl-caproic acid: $K_{NP\text{-}CAP}=1.2\ \mu M$).

A gene encoding a variable domain $HuV_{NP}$, comprising the B1-8 CDRs and the NEWM framework regions, was constructed by gene synthesis as follows.

The amino acid sequence of the $V_H$ domain of NEWM is shown in FIG. 2, wherein it is compared to the amino acid sequence of the $V_H$ domain of the B1-8 antibody. The sequence is divided into framework regions and CDRs according to Kabat et al. (loc. cit.). Conserved residues are marked with a line.

The amino acid and nucleotide sequence of the $HuV_{NP}$ gene, in which the CDRs from the B1-8 antibody alternate with the framework regions of the NEWM antibody, is shown in FIG. 3. The $HuV_{NP}$ gene was derived by replacing sections of the $MoV_{NP}$ gene in the vector pSV-$V_{NP}$ (see Neuberger, M. S., Williams, G. T., Mitchell, E. B., Jouhal, S., Flanagan, J. G. and Rabbitts, T. H., Nature, 314, 268–270, 1985) by a synthetic fragment encoding the $HuV_{NP}$ domain. Thus the 5' and 3' non-coding sequences, the leader sequence, the L-V intron, five N-terminal and four C-terminal amino acids are from the $MoV_{NP}$ gene and the rest of the coding sequence is from the synthetic $HuV_{NP}$ fragment.

The oligonucleotides from which the $HuV_{NP}$ fragment was assembled are aligned below the corresponding portion of the $HuV_{NP}$ gene. For convenience in cloning, the ends of oligonucleotides 25 and 26b form a Hind II site followed by a Hind III site, and the sequences of the 25/26b oligonucleotides therefore differ from the HuV$_{NP}$ gene.

The HuV$_{NP}$ synthetic fragment was built as a PstI-Hind III fragment. The nucleotide sequence was derived from the protein sequence using the computer programme ANALYSEQ (Staden, R., Nuc. Acids. Res., 12, 521–538, 1984) with optimal codon usage taken from the sequences of mouse constant domain genes. The oligonucleotides (1 to 26b, 28 in total) vary in size from 14 to 59 residues and were made on a Biosearch SAM or an Applied Biosystems machine, and purified on 8M-urea polyacrylamide gels (see Sanger, F. and Coulson, A., FEBS Lett., 87, 107–110, 1978).

The oligonucleotides were assembled in eight single stranded blocks (A–D) containing oligonucleotides [1,3,5,7] (Block A), [2,4,6,8] (block A'), [9,11,13a,13b] (Block B), [10a, 10b,12/14] (block B'), [15, 17] (block C), [16,18] (block C'), [19, 21, 23, 25] (block D) and [20, 22/24, 26a, 26b] (block D').

I a typical assembly, for example of block A, 50 pmole of oligonucleotides 1,3,5 and 7 were phosphorylated at the 5' end with T4 polynucleotide kinase and mixed together with 5 pmole of the terminal oligonucleotide [1] which had been phosphorylated with 5 $\mu$Ci [$\gamma$-$^{32}$p] ATP (Amersham 3000 Ci/mmole). These oligonucleotides were annealed by heating to 80° C. and cooling over 30 minutes to room temperature, with unkinased oligonucleotides 2, 4 and 6 as splints, in 150 $\mu$l of 50 mM Tris.Cl, pH 7.5, 10 mM MgCl$_2$. For the ligation, ATP (1 mM) and DTT (10 mM) were added with 50 U T4 DNA ligase (Anglian Biotechnology Ltd.) and incubated for 30 minutes at room temperature. EDTA was added to 10 mM, the sample was extracted with phenol, precipitated from ethanol, dissolved in 20 $\mu$l water and boiled for 1 minute with an equal volume of formamide dyes. The sample was loaded onto and run on a 0.3 mm 8 m-urea 10% polyacrylamide gel. A band of the expected size was detected by autoradiography and eluted by soaking.

Two full length single strands were assembled from blocks A to D and A' to D' using splint oligonucleotides. Thus blocks A to D were annealed and ligated in 30 $\mu$l as set out in the previous paragraph using 100 pmole of oligonucleotides 10a, 16 and 20 as splints. Blocks A' to D' were ligated using oligonucleotides 7, 13b and 17 as splints.

After phenol/ether extraction, block A–D was annealed with block A'–D', small amounts were cloned in the vector M13mp18 (Yanish-Perron, C., Vieira, J. and Messing, J., Gene, 33, 103–119, 1985) cut with PstI and Hind III, and the gene sequenced by the dideoxy technique (Sanger, F., Nicklen, S. and Coulson, A. R., PNAS USA, 74, 5463–5467, 1977). The MoV$_{NP}$ gene was transferred as a Hind III-BamHI fragment from the vector pSV-V$_{NP}$ (Neuberger et al., loc. cit.) to the vector M13mp8 (Messing, J. and Vieira, J., Gene, 19, 269–276, 1982). To facilitate the replacement of MoV$_{NP}$ coding sequences by the synthetic HuV$_{NP}$ fragment, three Hind II sites were removed from the 5' non-coding sequence by site directed mutagenesis, and a new Hind II site was subsequently introduced near the end of the fourth framework region (FR4 in FIG. 2). By cutting the vector with PstI and Hind II, most of the V$_{NP}$ fragment can be inserted as a PstI-Hind II fragment. The sequence at the Hind II site was corrected to NEWM FR4 by site directed mutagenesis.

The Hind III-Bam HI fragment, now carrying the HuV$_{NP}$ gene, was excised from M13 and cloned back into pSV-V$_{NP}$ to replace the MoV$_{NP}$ gene and produce a vector pSV-HuV$_{NP}$. Finally, the genes for the heavy chain constant domains of human Ig E (Flanagan, J. G. and Rabbitts, T. H., EMBO J., 1, 655–660, 1982) were introduced as a Bam HI fragment to give the vector pSV-HuV$_{NP}$.HE. This was transfected into the myeloma line J558 L by spheroplast fusion.

The sequence of the HuV$_{NP}$ gene in pSV-HuV$_{NP}$.HE was checked by recloning the Hind III-Bam HI fragment back into M13mp8 (Messing et al., loc. cit.). J558L myeloma cells secrete lambda 1 light chains which have been shown to associate with heavy chains containing the MoV$_{NP}$ variable domain to create a binding site for NP-cap or the related hapten NIP-Cap (3-iodo-4-hydroxy-5-nitrophenylacetylcaproic acid) (Reth, M., Hammerling, G. J. and Rajewsky, K., Eur. J. Immunol., 8, 393–400, 1978).

As the plasmid pSV-HuV$_{NP}$.HE contains the gpt marker, stably transfected myeloma cells could be selected in a medium containing mycophenolic acid. Transfectants secreted an antibody (HuV$_{NP}$-IgE) with heavy chains comprising a HuV$_{NP}$ variable domain (i.e. a "humanised" mouse variable region) and human $\epsilon$ constant domains, and lambda 1 light chains from the J558L myeloma cells.

The culture supernatants of several gpt$^+$ clones were assayed by radioimmunoassay and found to contain NIP-cap binding antibody. The antibody secreted by one such clone was purified from culture supernatant by affinity chromatography on NIP-cap Sepharose (Sepharose is a registered trade mark). A polyacrylamide-SDS gel indicated that the protein was indistinguishable from the chimeric antibody MoV$_{NP}$-IgE (Neuberger et al., loc. cit.).

The HuV$_{NP}$-IgE antibody competes effectively with the MoV$_{NP}$-IgE for binding to both anti-human-IgE and to NIP-cap coupled to bovine serum albumin.

Various concentrations of HuV$_{NP}$-IgE and MoV$_{NP}$-IgE were used to compete the binding of radiolabelled MoV$_{NP}$-IgE to polyvinyl microtitre plates coated with (a) Sheep anti-human-IgE antiserum (Seward Laboratories); (b) NIP-cap-bovine serum albumin; (c) Ac38 anti-idiotypic antibody; (d) Ac 146 anti-idiotypic antibody; and (e) rabbit anti-MoV$_{NP}$ antiserum. Binding was also carried out in the presence of MoV$_{NP}$-IgM antibody (Neuberger, M. S., Williams, G. T. and Fox, R. O., Nature, 312, 604–608, 1984) or of JW5/1/2 which is an IgM antibody differing from the MoV$_{NP}$-IgM antibody at 13 residues mainly located in the V$_H$ CDR2 region.

Figure 4:
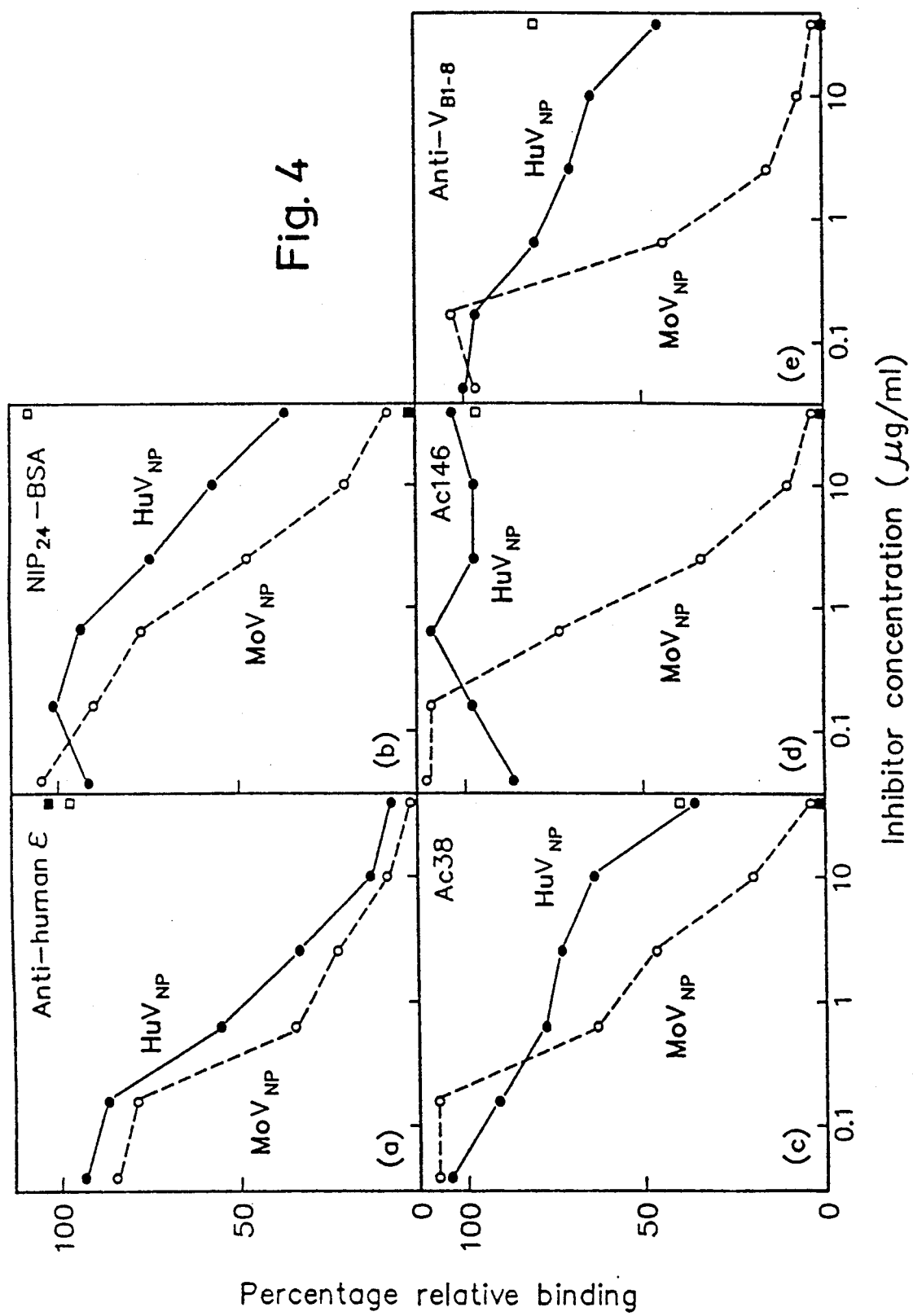
FIG. 4 shows a comparison of the results for $HuV_{NP}$-IgE and $MoV_{NP}$-IgE in binding inhibition assays.

The results of the binding assays are shown in FIG. 4, wherein black circles represent HuV$_{NP}$, white circles MoV$_{NP}$, black squares MoV$_{NP}$-IgM and white squares JW5/1/2. Binding is given relative to the binding in the absence of the inhibitor.

The affinities of HuV$_{NP}$-IgE for NP-cap and NIP-cap were then measured directly using the fluorescence quench technique and compared to those for MoVNP-IgE, using excitation at 295 nm and observing emission at 340 nm (Eisen, H. N., Methods Med. Res., 10, 115–121,1964).

Antibody solutions were diluted to 100 nm in phosphate buffered saline, filtered (0.45 um pore cellulose acetate) and titrated with NP-cap in the range 0.2 to 20 $\mu$M. As a control, mouse DI-3 antibody (Mariuzza, R. A., Jankovic, D. L., Bulot, G., Amit, A. G., Saludjian, P., Le Guern, A., Mazie, J. C. and Poljak, R. J., J. Mol.

Biol., 170, 1055-1058, 1983), which does not bind hapten, was titrated in parallel.

Decrease in the ratio of the fluorescence of HuV$_{NP}$-IgE or HuV$_{NP}$-IgE to the fluorescence of the D1-3 antibody was taken to be proportional to NP-cap occupancy of the antigen binding sites. The maximum quench was about 40% for both antibodies, and hapten dissociation constants were determined from least-squares fits of triplicate data sets to a hyperbola.

For NIP-cap, hapten concentration varied from 10 to 300 nM, and about 50% quenching of fluorescence was observed at saturation. Since the antibody concentrations were comparable to the value of the dissociation constants, data were fitted by least squares to an equation describing tight binding inhibition (Segal, I. H., in "Enzyme Kinetics", 73-74, Wiley, N.Y., 1975).

The binding constants obtained from these data for these antibodies are shown in Table 1 below.

TABLE 1

|  | K$_{NP-cap}$ | K$_{NIP-cap}$ |
|---|---|---|
| MoV$_{NP}$-IgE | 1.2 μM | 0.02 μM |
| HuV$_{NP}$-IgE | 1.9 μM | 0.07 μM |

These results show that the affinities of these antibodies are similar and that the change in affinity is less than would be expected for the loss of a hydrogen bond or a van der Waals contact point at the active site of an enzyme.

Thus, it has been shown that it is possible to produce an antibody variable domain having human framework regions and mouse CDRs without any significant loss of antigen binding capacity.

As shown in FIG. 4(d), the HuV$_{NP}$-IgE antibody has lost the MoV$_{NP}$idiotypic determinant recognised by the antibody Ac146. Furthermore, HuV$_{NP}$-IgE also binds the Ac38 antibody less well (FIG. 4(c)), and it is therefore not surprising that HuV$_{NP}$-IgE has lost many of the determinants recognised by the polyclonal rabbit anti-idiotypic antiserum (FIG. 4(e)).

It can thus be seen that, although the HuV$_{NP}$-IgE antibody has acquired substantially all the antigen binding capacity of the mouse CDRs, it has not acquired any substantial proportion of the mouse antibody's antigenicity.

The results of FIGS. 4(d) and 4(e) carry a further practical implication. The mouse (or human) CDRs could be transferred from one set of human frameworks (antibody 1) to another (antibody 2). In therapy, anti-idiotypic antibodies generated in response to antibody 1 might well bind poorly to antibody 2. Thus, as the anti-idiotypic response starts to neutralise antibody 1 treatment could be continued with antibody 2, and the CDRs of a desired specificity used more than once.

Similar work has now been carried out using primer-directed, oligonucleotide site-directed mutagenesis using three synthetic oligonucleotides coding for each of the mouse CDRs and the flanking parts of framework regions to produce a variable domain gene similar to the HuV$_{NP}$ gene.

In this work, the nucleotide sequence of a mouse antibody (D1.3) to hen egg-white lysozyme was determined after cloning the cDNA. Three synthetic oligonucleotides were then designed to introduce the D1.3 V$_H$CDRs in place of the V$_H$CDRs of the HuV$_{NP}$ gene. The Hu$_{NP}$ gene has been cloned into M13mp8 as a BamHI-HindIII fragment, as described above. Each oligonucleotide has 12 nucleotides at the 5' end and 12 nucleotides at the 3' end which are complementary to the appropriate HuV$_{NP}$ framework regions. The central portion of each oligonucleotide encodes either CDR1, CDR2, or CDR3 of the D1.3 antibody, as shown in FIG. 5, to which reference is now made. It can be seen from this Figure that these oligonucleotides are 39, 72 and 48 nucleotides long respectively.

10 pmole of D1.3 CDR1 primer was phosphorylated at the 5' end and annealed to 1μg of the M13-HuV$_{NP}$ template and extended with the Klenow fragment of DNA polymerase in the presence of T4 DNA ligase. After an oligonucleotide extension at 15° C., the sample was used to transfect E. coli strain BHM71/18 mutL and plaques gridded and grown up as infected colonies.

After transfer to nitrocellulose filters, the colonies were probed at room temperature with 10 pmole of D1.3 CDR1 primer labelled at the 5' end with 30 μCi$^{32}$-p-ATP. After a 3" wash at 60° C., autoradiography revealed about 20% of the colonies had hybridised well to the probe. All these techniques are fully described in "Oligonucleotide site-directed mutagenesis in M13" an experimental manual by P. Carter, H. Bedouelle, M. M. Y. Waye and G. Winter 1985 and published by Anglian Biotechnology Limited, Hawkins Road, Colchester, Essex CO2 8JX. Several clones were sequenced, and the replacement of HuV$_{NP}$ CDR1 by D.13 CDR1 was confirmed. This M13 template was used in a second round of mutagenesis with D1.3 CDR2 primer; finally template with both CDRs 1&2 replaced was used in a third round of mutagenesis with D.13 CDR3 primer. In this case, three rounds of mutagenesis were used. However, the three CDR oligonucleotides can be annealed together, and the triple mutant constructed in a single step.

What I claim is:

1. An altered antibody or antigen-binding fragment thereof, wherein a variable domain of the antibody or antigen-binding fragment has the framework regions of a first immunoglobulin heavy or light chain variable domain and the complementarity determining regions of a second immunoglobulin heavy or light chain variable domain, wherein said second immunoglobulin heavy or light chain variable domain is different from said first immunoglobulin heavy or light chain variable domain in antigen binding specificity, antigen binding affinity, species, class or subclass.

2. The altered antibody or antigen-binding fragment thereof set forth in claim 1, wherein said complementarity determining regions correspond to the complementarity determining regions of a rodent immunoglobulin heavy or light chain.

3. The altered antibody or antigen-binding fragment thereof set forth in claim 2, wherein said rodent is a mouse.

4. The altered antibody or antigen-binding fragment thereof set forth in claim 1, wherein said framework regions of said first immunoglobulin heavy or light chain variable domain correspond to the framework regions of a human heavy or light chain.

5. The altered antibody or antigen-binding fragment thereof set forth in claim 1, wherein said framework regions of said first immunoglobulin heavy or light chain variable domain correspond to the framework regions of a human immunoglobulin heavy or light chain and said complementarity determining regions of said second immunoglobulin heavy or light chain variable domain correspond to the complementarity determining regions of a rodent immunoglobulin heavy or light chain.

6. The altered antibody or antigen-binding fragment thereof set forth in claim 5, wherein said rodent is a mouse.

7. A method of producing an altered antibody comprising the steps:
   (a) preparing a eukaryotic expression vector comprising a promoter operably linked to a DNA sequence which encodes an immunoglobulin heavy or light chain, wherein the variable domain of said immunoglobulin heavy or light chain comprises the framework regions of a first immunoglobulin heavy or light chain variable domain and the complementarity determining regions of a second heavy or light chain variable domain, and wherein said second immunoglobulin heavy or light chain variable domain is different from said first immunoglobulin heavy or light chain variable domain in antigen binding specificity, antigen binding affinity, species, class or subclass;
   (b) transforming a cell line with said expression vector;
   (c) culturing said transformed cell line to produce said altered antibody; and,
   (d) recovering said altered antibody.

8. The method of producing an altered antibody as set forth in claim 7, wherein said framework regions of said first immunoglobulin heavy or light chain correspond to the framework regions of human immunoglobulin heavy or light chain variable domain and said complementarity determining regions of said second immunoglobulin heavy or light chain variable domain correspond to the complementarity determining regions of rodent immunoglobulin heavy or light chain.

9. The method of producing an altered antibody as set forth in claim 8, wherein said rodent is a mouse.

10. The method of producing an altered antibody as set forth in claim 7, wherein said expression vector is a replicable expression vector.

11. The method of producing an altered antibody as set forth in claim 7, wherein said cell line is an immortalized cell line.

12. The method of producing an altered antibody as set forth in claim 7, wherein said cell line is a myeloma cell line.

13. A method of producing an altered antibody comprising the steps:
   (a) preparing a first eukaryotic expression vector comprising a promoter operably linked to a DNA sequence which encodes an immunoglobulin heavy chain, wherein the variable domain of said immunoglobulin heavy chain comprises the framework regions of a first immunoglobulin heavy chain variable domain and the complementarity determining regions of a second heavy chain variable domain, and wherein said second immunoglobulin heavy chain variable domain is different from said first immunoglobulin heavy chain variable domain in antigen binding specificity, antigen binding affinity, species, class or subclass;
   (b) preparing a second eukaryotic expression vector comprising a promoter operably linked to a DNA sequence which encodes an immunoglobulin light chain, wherein the variable domain of said immunoglobulin light chain comprises the framework regions of a first immunoglobulin light chain variable domain and the complementarity determining regions of a second light chain variable domain, and wherein said second immunoglobulin light chain variable domain is different from said first immunoglobulin light chain variable domain in antigen binding specificity, antigen binding affinity, species, class or subclass;
   (c) transforming a cell line with said first and second expression vectors;
   (d) culturing said transformed cell line to produce said altered antibody; and,
   (e) recovering said altered antibody.

14. An altered antibody produced by the method of claim 7.

15. An altered antibody produced by the method of claim 13.

16. A eukaryotic expression vector for expression of an altered antibody comprising a DNA sequence encoding an immunoglobulin heavy or light chain, wherein the variable domain has the framework regions of a first immunoglobulin heavy or light chain variable domain and the complementarity determining regions of a second immunoglobulin heavy or light chain variable domain, and wherein said second immunoglobulin heavy or light chain variable domain is different from said first immunoglobulin heavy or light chain variable domain in antigen binding specificity, antigen binding affinity, species, class or subclass.

17. The expression vector set forth in claim 16, wherein said DNA encodes an immunoglobulin heavy chain.

18. The expression vector set forth in claim 16, wherein said DNA sequence encodes an immunoglobulin light chain.

19. The expression vector set forth in claim 16, wherein said framework regions correspond to human immunoglobulin heavy or light chain framework regions.

20. The expression vector set forth in claim 16, wherein said complementarity determining regions correspond to rodent immunoglobulin heavy or light chain complementarity determining regions.

21. The expression vector set forth in claim 20, wherein said rodent is a mouse.

22. A host cell transformed with the vector of claim 16.

23. A cell line producing the altered antibody or antigen-binding fragment thereof of claim 1.

* * * * *

UNITED STATES PATENT AND TRADEMARK OFFICE
CERTIFICATE OF CORRECTION

PATENT NO.   :   5,225,539

DATED        :   July 6, 1993

INVENTOR(S)  :   Gregory P. Winter

It is certified that error appears in the above-identified patent and that said Letters Patent is hereby corrected as shown below:

On the Title Page:

[63]   The filing date of related U.S. Application Serial No. 903,776, "Mar. 27, 1986", should read --Sep. 4, 1986--.

Signed and Sealed this

Second Day of August, 1994

Attest:

BRUCE LEHMAN

Attesting Officer        Commissioner of Patents and Trademarks